United States Patent [19]

Bredesen

[11] Patent Number: 5,681,711
[45] Date of Patent: Oct. 28, 1997

[54] METHOD FOR PROMOTING APOPTOSIS IN MAMMALIAN NEUAL CELLS

[75] Inventor: Dale E. Bredesen, Rancho Santa Fe, Calif.

[73] Assignee: University of California-Los Angeles, Los Angeles, Calif.

[21] Appl. No.: 411,011

[22] Filed: Mar. 27, 1995

[51] Int. Cl.$^6$ .............................. C12N 5/08; C12N 15/09; C12Q 1/02
[52] U.S. Cl. ......................... 435/29; 435/172.3; 435/368
[58] Field of Search .............................. 435/69.1, 240.2, 435/29, 172.3

[56] References Cited

PUBLICATIONS

Zhong et al., "bcl–2 Inhibits Death of Central Neural Cells Induced by Multiple Agents", Proceedings of the National Academy of Sciences USA, vol. 90, pp. 4533–4537, May 1993.

Borchelt et al., "Superoxide Dismutase 1 With Mutations Linked to Familial Amyotrophic Lateral Sclerosis Possesses Significant Activity", Proceedings of the National Academy of Sciences USA, vol. 91, pp. 8292–8296, Aug. 1994.

Gurney et al., "Motor Neuron Degeneration in Mice That Express a Human Cu,Zn Superoxide Dismutase Mutation", Science, vol. 264, pp. 1772–1775, Jun. 17, 1994.

*Primary Examiner*—George G. Elliott
*Assistant Examiner*—Amy J. Nelson
*Attorney, Agent, or Firm*—Gray Cary Ware & Freidenrich; Stephen E. Reiter

[57] ABSTRACT

A method for determining whether a compound inhibits apoptosis induction in neural cells expressing a FALS-associated sod-1 mutant. A neural cell culture is provided having a plurality of neural cells expressing a FALS-associated sod-1 mutant, wherein through the expression of the sod-1 mutant, the neural cells have a low resistance to apoptosis induction. The neural cell culture is treated with a substance to form a modified cell culture and apoptosis is induced in the modified cell culture. The modified cell culture is then assayed to determine whether it has a higher resistance to apoptosis induction than the untreated neural cell culture. The method is useful in screening substances for use as potential drugs for treating ALS.

5 Claims, 3 Drawing Sheets

METHOD FOR PROMOTING APOPTOSIS IN MAMMALIAN NEUAL CELLS

BACKGROUND OF THE INVENTION

1. Field of the Invention

The present invention relates generally to amyotrophic lateral sclerosis (ALS). More particularly, the present invention relates to ALS and cell culture models which can be used to investigate ALS and screen substances to identify those which should be tested further as potential drugs against ALS.

2. Description of the Related Art

The publications and other reference materials referred to herein to describe the background of the invention and to provide additional detail regarding its practice are hereby incorporated by reference. For convenience, the reference materials are numerically referenced and grouped in the appended bibliography.

Amyotrophic lateral sclerosis (ALS) is a neurodegenerative disease with an incidence of approximately one in ten thousand. Approximately 10% of cases of ALS are familial (FALS), and in a subset of these cases, mutations in sod-1, which encodes copper/zinc superoxide dismutase (CuZnSOD), have been demonstrated (1). It has been hypothesized that the mutations in sod-1 lead to FALS by decreasing the enzymatic activity of CuZnSOD (2). However, several findings have raised questions about this interpretation.

First, the determinations of low CuZnSOD activity were carried out in vitro, in some cases following isolation of the protein in non-physiological conditions, without correlation of in vivo activity (2, 3). Second, the FALS-associated sod-1 mutations affect amino acid residues involved in enzyme dimerization or β-barrel turns, rather than those corresponding to active site (1–4). Third, all mutations identified to date have been missense, rather than nonsense, mutations (1–4). Fourth, it is unusual for a null or hypomorphic mutation to lead to a dominantly inherited disease when the mutated gene encodes an enzyme (6). Fifth, SOD activity measurements from lymphoblasts of patients with the G37R mutation have demonstrated normally active heterodimeric CuZnSOD, implying that at least for the G37R mutation, the total SOD activity is not compromised by heterodimerization of the wild type monomer with the mutant monomer (7). Sixth, transgenic mice expressing the G93A mutation demonstrate motor neuron degeneration despite an increased level of superoxide dismutase activity (8). As is apparent from the foregoing, the mechanisms and causes of ALS remain unknown. It would be very useful to provide a method which could be used to screen for potentially therapeutic compounds for this currently untreatable and virtually uniformly fatal illness. There is currently no way to do this; transgenic mice with ALS have been generated by several laboratories, but it is not practical to use mice as an initial model to screen thousands of drugs for their potential efficacy against ALS.

In view of the above, there is presently a need to develop a system or procedure which can be used to quickly and easily screen a variety of drugs to determine their potential usefulness in treating ALS. In addition, it would be desirable if the procedure could also be used to investigate the mechanisms by which ALS leads to neuro degeneration.

SUMMARY OF THE INVENTION

FALS-associated sod-1 mutants promote, rather than inhibit neural apoptosis, in a dominant fashion, when introduced into mammalian neural cells, despite the fact that these mutants retain enzymatic SOD activity in mammalian neural cells. This finding, made in accordance with the present invention, dissociates the mutants' SOD activity from their effect on neural cell death, indicating that FALS associated with sod-1 mutations is not simply the result of a decrease in CuZnSOD enzymatic function. Accordingly, neural cells which express FALS-associated sod-1 mutants are used in accordance with the present invention as a cell model to provide an initial screening of a wide variety of compounds to determine their potential usefulness as a drug for treating ALS. Compounds which are found to decrease the apoptosis rate for neural cells expressing FALS-associated sod-1 mutants are candidates for further screening and subsequent testing for potential effectiveness against ALS.

As a feature of the present invention, a method is provided for determining whether a substance or compound inhibits apoptosis induction in neural cells expressing a FALS-associated sod-1 mutant. The method involves providing a neural cell culture comprised of a plurality of neural cells expressing a FALS-associated sod-1 mutant, wherein through the expression of the sod-1 mutant, the neural cells have a low resistance to apoptosis induction; treating the neural cell culture with a drug to provide a modified cell culture; inducing apoptosis in the modified cell culture; and assaying whether the modified cell culture has a higher resistance to apoptosis than the untreated neural cell culture.

As another feature of the present invention a kit for determining whether a drug inhibits apoptosis induction in a neural cell culture having a plurality of neural cells expressing a FALS-associated sod-1 mutant is presented.

The sod-1 modified cell cultures are not only useful in screening compounds for potential ALS treatment efficacy, but they are also useful as a cell model for investigating ALS in order to provide an understanding of the pathophysiology of this disease.

The ALS drug screening method provided in accordance with the present invention is intended to be used as a first step in the identification of potential ALS drugs. Of the many different compounds which are screened, only those which are found to be effective in reducing the apoptosis of the sod-1 modified cell culture are subjected to further confirmatory testing, such as use in actual treatment of ALS animal models.

The above discussed and many other features and attendant advantages of the present invention will become better understood by reference to the following detailed description when taken in conjunction with the accompanying drawings.

DETAILED DESCRIPTION OF THE PREFERRED EMBODIMENTS

Figure 1A:
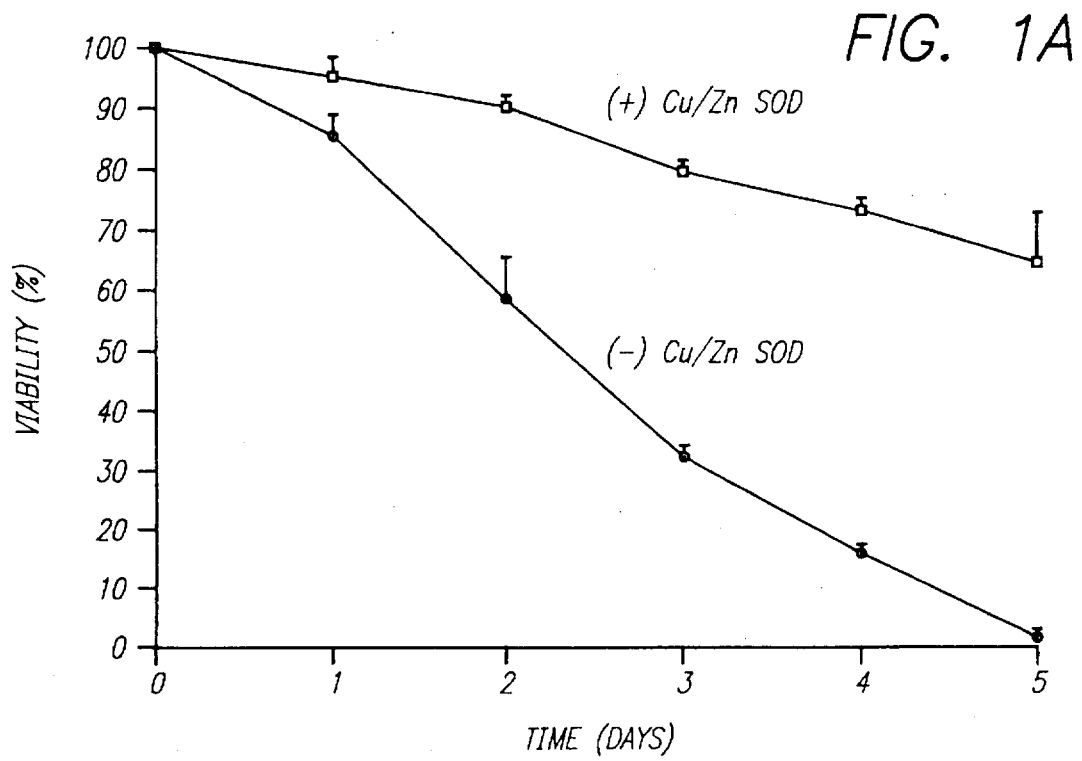
FIG. 1A is a graphical representation of the inhibition of apoptosis by the over-expression of CuZnSOD in conditionally-immortalized neural cells treated with calcium ionophore A23187 (1 μM).

As a feature of the present invention, a method is presented for determining whether a drug inhibits apoptosis in neural cells expressing a sod-1 mutant. The method involves the steps of providing a neural cell culture which constitutes a plurality of neural cells expressing a FALS-associated sod-1 mutant such that the neural cells have a low resistance to apoptosis induction; treating the neural cell culture with a substance to form a modified cell culture; inducing apoptosis in the modified cell culture; and assaying whether the modified cell culture has a higher resistance to apoptosis induction than the neural cell culture.

Neural cells employed in accordance with the present invention are preferably CSM14.1 temperature-sensitive immortalized rat nigral neural cells. Other neural cells may be used and even non-neural cells may be used. Suitable non-neural cells include NIH 3T3 fibroblasts. The use of non-neural cells may lessen the magnitude of the effect. Although either neural or non-neural cells may be used, neural cells are preferred. The following description will be directed to a description of the present invention with respect to neural cells with it being understood that the invention is not so limited.

The neural cells are transformed using conventional techniques to form cell cultures which express a sod-1 mutant. These sod-1 mutant expressing cells demonstrate a reduced resistance to apoptosis. Apoptosis, a programmed cell death, is a form of cell death in which the cell participates actively, through an endogenous suicide program. It can be induced by many different stimuli, such as calcium ionophores, withdrawal of growth factors or serum, certain hormones (depending on cell type), oxidants, free radical inducing agents, heat, etoposide, staurosporine and mitochondrial toxins. Apoptosis is characterized by an alteration in morphology, including: (1) cell rounding and retraction of processes; (2) budding off of cellular contents; (3) zeiosis; (4) chromatin condensation; (5) nuclear fragmentation. Fragmentation of DNA—initially to the 50–300 kb range, then in 180 base pair multiples—nearly always occurs.

Neural cells expressing a FALS-associated sod-1 mutant are preferably prepared by transforming neural cells with a gene having a FALS-associated sod-1 mutant coding sequence. The gene used to transform the cells includes any sequences necessary to express the product of the coding sequence such as, but not limited to, a promoter, an enhancer, and a translation initiation sequence. Preferably, the gene constitutes a genomic clone of the FALS-associated sod-1 mutant. Alternatively, a cDNA of the sod-1 mutant coding sequence may be linked to a heterologous promoter capable of expressing the coding sequence in the neural cells.

Methods of transforming mammalian cells and neural cells are well known (17). The gene harboring the FALS-associated sod-1 mutant coding sequence is preferably transfected into the neural cells in conjunction with a marker which allows for the identification of cells which have received the gene. The gene coding for the sod-1 mutant may be part of a plasmid or virus which contains the marker. Preferably the marker is a gene imparting neomycin or other antibiotic resistance which allows for the selection of successful transformed cells via drugs. For the mutant sod-1 to enhance apoptosis, it should be expressed at least as highly as the endogenous sod-1. For the wild-type sod-1 to inhibit apoptosis in CSM14.1 cells requires 3-fold over-expression or greater (other cells may vary in their response to the over-expression of wild-type sod-1).

The FALS-associated sod-1 mutant coding sequence used to transform neural cells in accordance with the present invention is required to decrease the resistance of the cells to apoptosis induction. Preferably, mutants A4V, G37R or G41D are used. All three of these mutants have the same effect on neural cells, i.e. decrease in resistance to apoptosis. This is the opposite effect of wild-type sod-1. Since all three mutants have the same effect, it is expected other mutants will also have the same effect.

Neural cells expressing the sod-1 mutant are treated with the substance being screened to form a modified cell culture. Substances which may be used in accordance with the present invention include any compounds which may possibly have any inhibitory effect on apoptosis induction. The number and type of candidate substances or compounds is virtually unlimited since the invention is intended to be a screening procedure for potential anti-ALS activity. Methods for treating or exposing cell cultures, including neural cell cultures, to compounds are well known. The amount of substance added may be varied widely to establish activity levels for the substance. Preferred substances are compounds which are not overly toxic to humans and which are believed to have pharmacological activity.

Subsequent to induction of apoptosis in the modified cell culture, the culture is assayed to determine whether the modified cell culture has a higher resistance to the induction of apoptosis than the untreated neural cell culture. Assaying the degree of resistance of the modified cell culture to apoptosis induction is preferably done by measuring the level of survival of the cells in the modified cell culture after apoptosis induction and comparing that level to the level of survival of the untreated neural cell culture. If the substance tested inhibits the induction of apoptosis in neural cells expressing a sod-1 mutant which causes the cells to have a low resistance to apoptosis induction, the modified cell culture will have a higher resistance to apoptosis induction than the untreated neural cell culture. Cell death (apoptosis) is preferably measured by MTT or propidium assay (15).

Apoptosis is preferably induced by withdrawing serum from the modified cell culture or by exposing the cell culture to calcium ionophore A23187. Another aspect of the present invention is a kit for determining whether a drug inhibits apoptosis induction in neural cells expressing a sod-1 mutant. The kit is composed of a neural cell culture having a plurality of neural cells expressing a FALS-associated sod-1 mutant, wherein through the expression of the sod-1 mutant the neural cells have a low resistance to apoptosis induction. The kit may be used in accordance with the previously presented method for determining whether a drug inhibits apoptosis induction in neural cells expressing a sod-1 mutant.

The neural cell culture employed with respect to the kit is the same as disclosed with respect to the previously disclosed method. The kit typically will include the sod-1 mutant expressing neural cells plated out on a standard culture plate (e.g. 96-well plate). The various compounds to be tested are added to different wells. In addition, varying amounts of the same compound may be added to different wells. The cell cultures in each well are then assayed for inhibition of cell death at different times from 0 to five days after apoptosis induction. The first measurement of inhibition of cell death is done prior to apoptosis induction in order to provide a control.

Another feature of the present invention is a method for investigating the mechanism by which FALS-associated sod-1 mutants lead to neural cell death. This method involves the steps of determining whether the mutant promotes apoptosis in mammalian neural cells.

The step of determining whether the FALS-associated sod-1 mutant promotes apoptosis in mammalian neural cells involves the following steps: providing a neural cell culture constituting a plurality of neural cells, wherein the neural cells are resistant to apoptosis induction; transforming the cell culture with the gene having a FALS-associated sod-1 mutant coding sequence to form a modified cell culture constituting neural cells expressing the sod-1 mutant; and assaying whether the FALS-associated sod-1 mutant promotes apoptosis in the modified cell culture.

Examples of practice are as follows:

Materials and Methods

Cell Culture and Expression Constructs. CSM14.1 temperature-sensitive immortalized rat nigral neural cells (11) were co-transfected with PGSOD-SVneo (12), which includes the genomic clone for human wild type sod-1, PGSOD(A4V)-Svneo (7), or PGSOD(G37R)-Svneo (7); and pBabe-puro (13) at a 20:1 ratio. Following selection in puromycin (7 μg/ml), populations containing greater than 100 colonies were compared, in order to prevent the bias inherent in comparing single colonies (11,14). The activity of SOD was assessed by the 6-hydroxydopamine autoxidation inhibition assay (10). Induction and assessment of apoptosis in cultured neural cells were carried out as described previously (15).

Figure 1B:
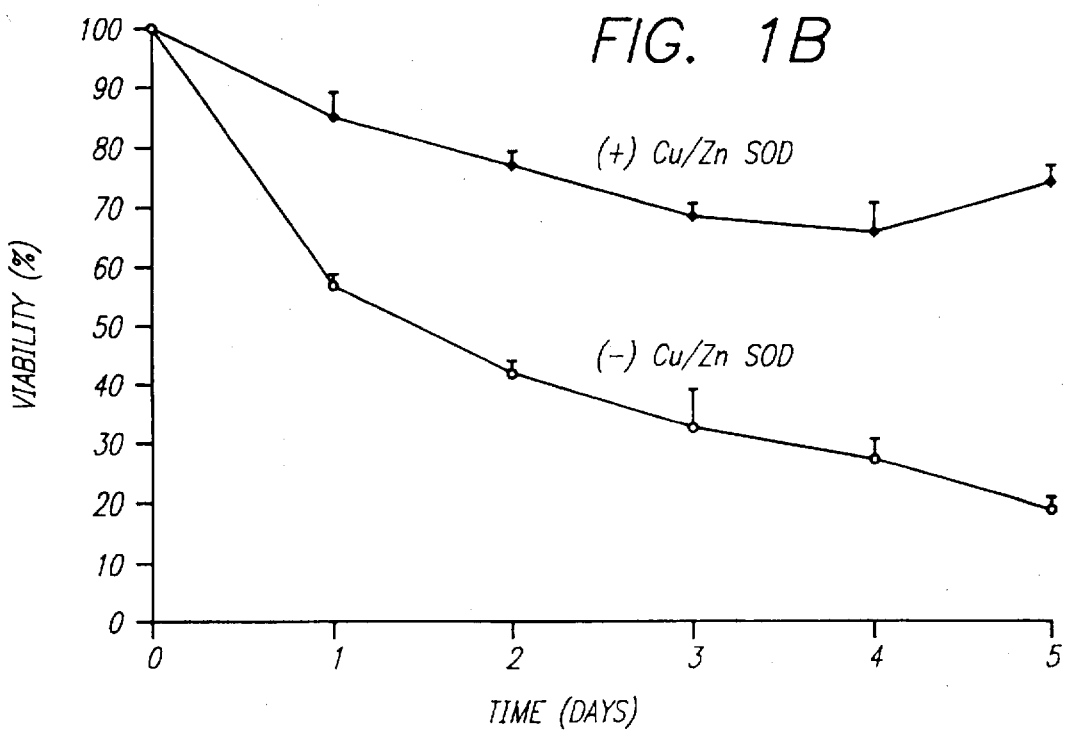
FIG. 1B is a graphical representation of the inhibition of apoptosis by the over-expression of CuZnSOD in conditionally immortalized neural cells after serum withdrawal.
Figure 2A:
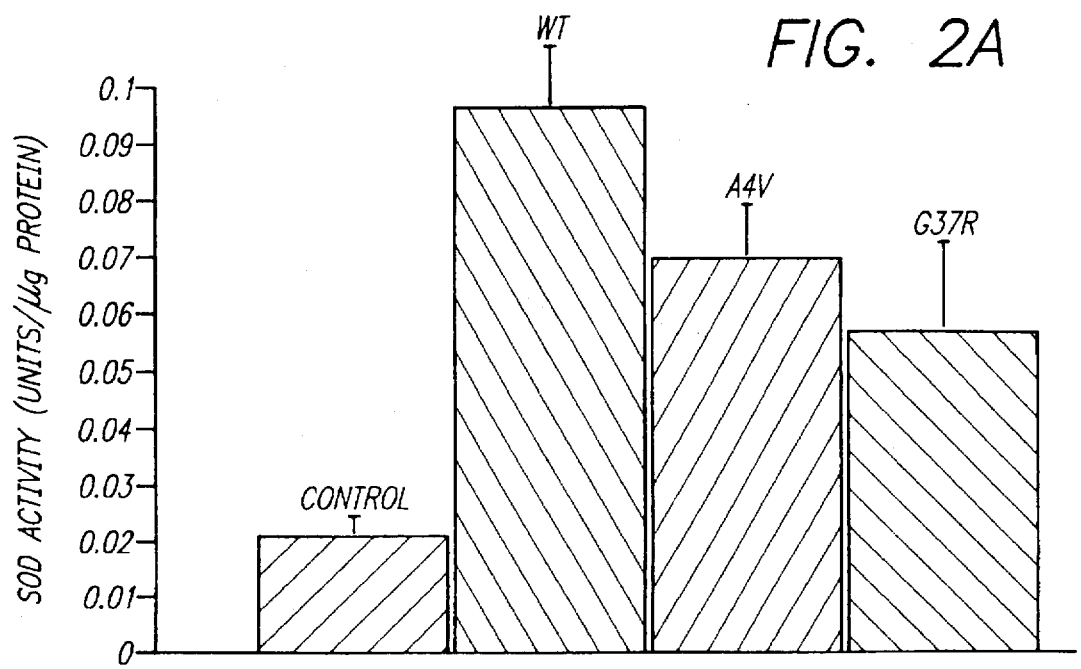
FIG. 2A is a bar graph depicting SOD activity of FALS-associated CuZnSOD mutants.
Figure 2B:
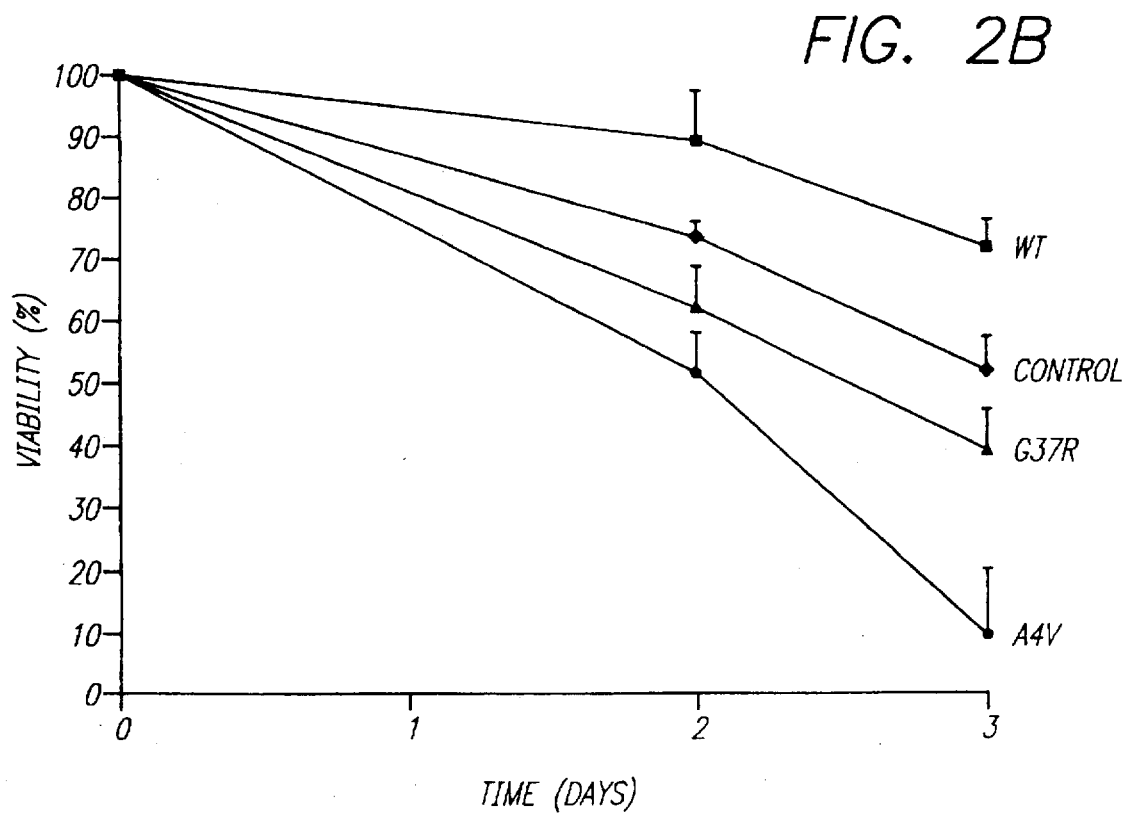
FIG. 2B is a graphical representation of the viability of CSM14.1 cells and transfectants after serum withdrawal.
Figure 2C:
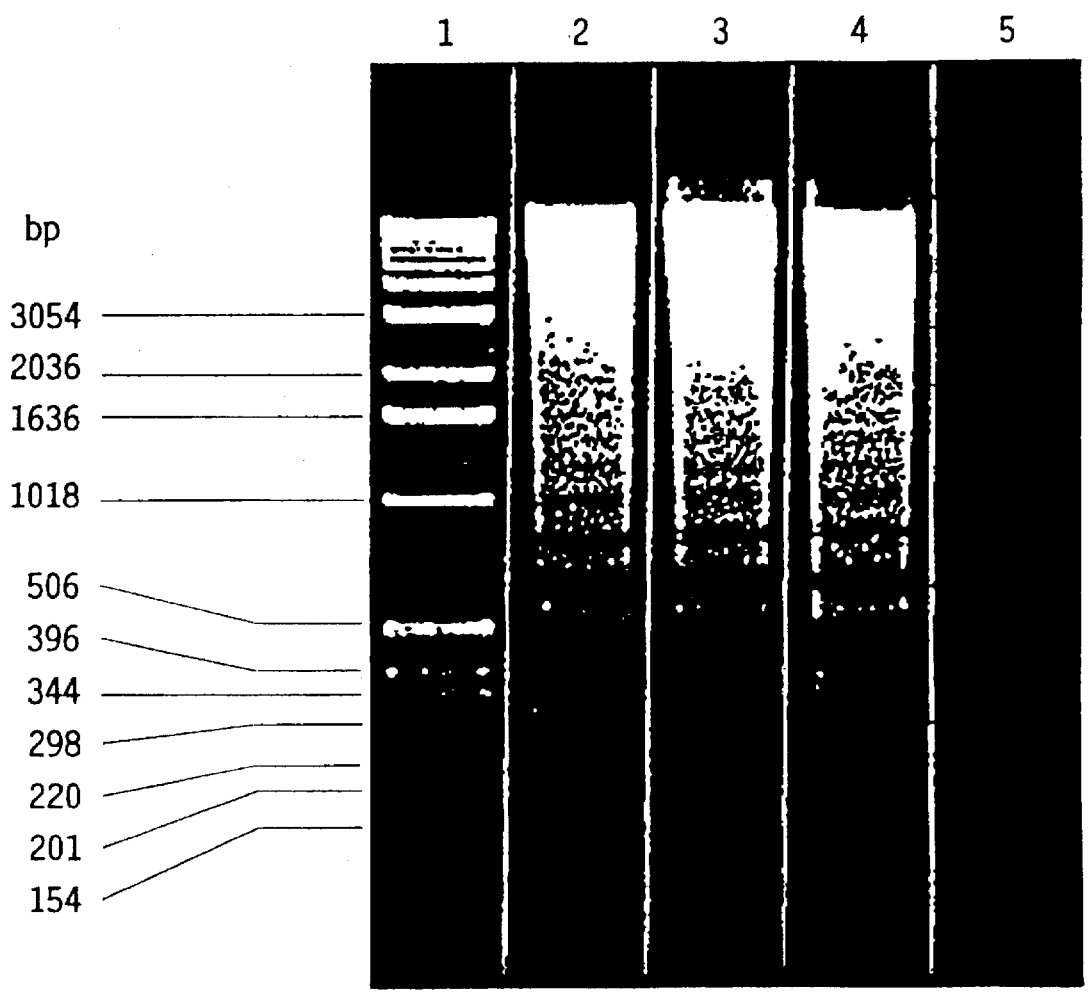
FIG. 2C depicts an agarose gel performed on genomic DNA isolated from neural cells.

Over-expression of Wildtype sod-1 in Neural Cells Inhibits Neural Apoptosis. Because of the retained enzymatic activity of the FALS-associated CuZnSOD mutants and the rescue of the sod-1 mutant yeast, the possibility that the FALS mutants might have an effect on neural survival independent of their effects on CuZnSOD activity was considered. The expression of bcl-2 in yeast mutants null for sod-1 has been shown to enhance their survival (16); bcl-2 expression has also been demonstrated to decrease the net cellular generation of reactive oxygen species (ROS) in mammalian neural cells (16) and inhibit lipid peroxidation in both hematopoietic and neural cells (16, 17). Therefore, the hypothesis that the over-expression of sod-1 would inhibit neural apoptosis was tested. The transfected CSM14.1 cells had a three-fold higher level of SOD activity than the control transfectants. This increase in SOD activity was associated with an inhibition of apoptosis, whether induced by serum withdrawal or the calcium ionophore A23187 (FIGS. 1 and 2). Inhibition of the activity of CuZnSOD with diethyldithiocarbamate (DDC; 2 mM) inhibited the anti-apoptotic effect of sod-1 over-expression in parallel: survival of CSM 14.1 cells over expressing CuZnSOD in serum-free medium for 6 days was reduced from 60±3% to 6±4% in DDC (2 mM) ($p<0.01$ by t-test, n=4). The viability of control transfectants was 29±4% in the absence of DDC, and 0 in the presence of DDC (2 mM). Paraquat (100 μM) reduced the viability of control transfectants in serum-containing medium from 94±5% to 43±8%, but not cells over expressing CuZnSOD (95±4% vs. 87±2%; $p>0.05$ by t-test, n=4).

FALS-Associated sod-1 Mutants Promote Neural Apoptosis. Two mutant sod-1 genes, A4V and G37R, were compared for their effects on SOD activity as well as on the inhibition of apoptosis in mammalian neural cells. Both of these mutations are associated with FALS, with the former being the most common sod-1 mutation observed in FALS (1). Protein extracts were prepared by glass bead lysis (23) and quantitated using the BioRad Protein Assay. SOD activity was assayed by measuring the effect of protein extracts on 6-hydroxydopamine autoxidation (10). Expression of each of the mutants led to an increase in SOD activity that was approximately 70% of that seen with the expression of the wild type sod-1 (FIG. 2A). The viability of CSM14.1 cells following the withdrawal of serum was determined. Cells transfected with the wild type sod-1 survived to a greater extent ($p.<0.05$ by 2-way analysis of variance; n=8) than the control cells; in contrast, the cells transfected with the G37R construct survived significantly less ($p<0.05$ by 2-way analysis of variance; n=8) than control cells, and cells transfected with A4V construct survived significantly less ($p<0.01$ by 2-way analysis of variance; n=8) than control cells. Each assay was repeated six times with different transfectants. Viability was measured as previously described. Thus, expression of each of the two mutants actually enhanced apoptosis in CSM14.1 cells (FIG. 2B).

That the sod-1 mutants promote apoptosis was further verified by the analysis of internucleosomal fragmentation which demonstrated DNA cleavage which is characteristic of apoptosis. Internucleosomal fragmentation DNA was observed (FIG. 2) in CSM 14.1 neural cells transfected with the control vector (lane 2), G37R (lane 3), or A4V (lane 4), but not in cells transfected with the vector expressing wild type human sod-1 (lane 15). In each case, DNA was extracted from $4 \times 10^6$ cells following 2 days in serum-free medium. Lane 1 contains a molecular weight marker (Boehringer Mannheim).

The present invention provides the first cell culture model of ALS which is useful for screening potentially therapeutic compounds for this currently untreatable illness and to hasten the finding of the underlying pathophysiology of ALS. The method of the present invention makes it possible and practical to screen thousands of compounds and identify those which are potentially effective against ALS. With the current model, one simply places the selected sod-1 mutant cells in cell culture plates (e.g. 96-well plates), adds the test compounds (each in a different well) and assays for an inhibition cell death. The assay is carried out by the MTT or propidium iodide assay or any of a number of standard assays, performed at times from 0 (control) to 5 days after apoptosis induction. Apoptosis induction may be by serum withdrawal, staurosporine, or the like. The few compounds that have an effect on cell death in this system represent excellent candidates for further screening in an ALS animal system such as the transgenic mouse system.

Having thus described the exemplary embodiments of the present invention, it should be noted by those skilled in the art that the disclosures herein are exemplary only and that various other alternations, adaption and modifications may be made within the scope of the present invention. Accordingly, the present invention is not limited to the specific embodiments as illustrated herein, but only by the following claims.

BIBLIOGRAPHY

1. Rosen, D. R. Siddique, T., Patterson, D., Figlewicz, D. A., Sapp, P., Hentaft, A., Donaldson, D., Goto, J., O'Regan, J. P., Deng, H., Rahmani, Z., Krizus, A., MaKenna-Yasek, D., Cayabyab, A., Gaston, S. M., Berger, R., Tanzi, R. E., Halperin, J. J., Herzfeldt, B., Van der Bergh, R., Hung, W., Bird, T., Deng, G., Mulder, D. W., Smyth, C., Laing, N. G., Soriano, E., Pericak-Vance,MA., Haines, J., Rouleau, G. A., Gusela, J. S., Horvitz, H. R., & Brown, R. H., Jr. (1993) *Nature* 362, 69–62.

2. Deng, H., Hentati, A., Talner, J. A., Igbal, Z., Cayabyab, A., Hung, W. Y., Getzoff, E. D., Hu, P., Herzfelt, B., Roos, R. P., Warner, C., Deng, G., Sofiano, E., Smyth, C., Parge, H. E., Ahmed, A., Roses, A. D., Hallewell, R. A., Pericak-Vance, M. A., & Sidique, T. (1993)*Science* 261, 1047–1051.

3. Bowling, A. C., Schultz, J. B., Brown, R. H., Jr. & Beal, M. F. (1993) *J. Neurochem*, 61, 2322–2325.
4. Robberecht, W., Sapp, P., Viaene, M. K., rosen, D., McKenna-Yasek, D., Haines, J., Hotritz, R., Theys, P., & Brown, R. H., Jr. (1994) *J. Neurochem.* 62, 384–387.
5. Osasawara, M., Matsubara, Y., Narisawa, K., Aoki, M., Nakamura, S., Itoyama, Y., & Abe, K. (1993) *Nature Genetics*, 5, 323–324.
6. E.-C Park & H. R. Horvitz (1986) *Genetics.* 113, 821–852.
7. Borchelt, D. R., Lee, M.,K., Slunt, H.S., Guamieri, M., Xu, Z., Wong, P.C., Brown, R. H., Jr., Price, D. L., Sisoidia, S. S., & Cleveland, D. W. *Proc. Natl. Acad. Sci. U.S.A.*, in press.
8. Gurney, M. E., Pu, H., Chiu, A. Y., Dal Canto, M. C., Polchow, C. Y., Alexander, D. C., Caliendo, J. Hentaft, A., Kwon, Y. W., Deng, H., Chen, W., Zhai, P., Sufit, R. L., & Siddique, T. (1994) *Science* 264, 1772–1775.
9. Hill, J. E., Myers, A. M. Koemer, T. J., & Tzagoloff, A. (1986) *Yeast* 2, 163–167.
10. Heikkila, R. E. & Felicitas, C. (1976) *Anal. Biochem.* 75, 356–362.
11. Zhong, L., Sarafian, T. A., Kane, D. J., Charles, A. C., Mah, S. P., Edwards, R. H., & Bredesen, D. E. (1993) *Proc. Natl. Acad. Sci. U.S.A.* 90, 4533–4537.
12. Lavanon, D., Lieman-Hurwitz, J., Dafni, N., Widgersen, M., Sherman, L., Bernstein, Y., Laver-Rudich, Z., Danciger, E., Stein, O, & Groner, Y. (1985) *EMBO J.* 4, 77–84.
13. Morgenstern, J. P. & Land, H. (1990) *Nucl. Acids Res.* 18, 3587–3596.
14. Rabizadeh, S., LaCount, D. J., Friesen, P. D., & Bredsen, D. E. (1993) *J. Neurochem.* 61, 2318–2321.
15. Kane, D. J., Sarafian, T. A., Anton, R. m, Hahn, H., Gralla, E. B., Valentine, J. S., Oral, T. & Bredesen, D. E. (1993) *Science* 262, 1274–1277.
16. Hockenbery, D., Oltavai, Z. N., Yin, X., Milliman, C. L. & Korsmeyer, S. J. (1993) *Cell* 75, 241–251.3.
17. Chu, G., Hayakawa, H., Berg, P., Electroporation for the efficient transfection fo mammalian cells with DNA, (1987) *Nuc. Acids Res.*, 15:1316–1326.

What is claimed is:

1. A method for screening a substance for potential efficacy as a drug for treating amytropic lateral sclerosis (ALS), said method comprising the steps of:

providing an untreated ALS cell culture model comprising a plurality of neural cells expressing a sod-1 mutant, wherein through the expression of said sod-1 mutant, said untreated ALS cell culture model has a low resistance to apoptosis induction;

treating said ALS cell culture model with a substance to form a treated ALS cell culture model;

inducing apoptosis in said treated ALS cell culture model;

determining whether said treated ALS cell culture model has a higher resistance to apoptosis induction than said untreated ALS cell culture model; and identifying said substance as having potential efficacy as a drug for treating ALS if said treated cell culture model is determined to have higher resistance to apoptosis induction than said untreated ALS cell culture model.

2. A method for screening a substance for potential efficacy as a drug for treating ALS according to claim 1, wherein said neural cells are transformed with a genomic clone of said sod-1 mutant.

3. A method for screening a substance for potential efficacy as a drug for treating ALS according to claim 1, wherein said sod-1 mutant is selected from the group consisting of A4V, G41D and G37R.

4. A method for screening a substance for potential efficacy as a drug for treating ALS according to claim 1, wherein said step of inducing apoptosis comprises withdrawing serum from said treated cell culture.

5. A method for screening a substance for potential efficacy as a drug for treating ALS according to claim 1, wherein said step of inducing apoptosis comprises exposing said modified cell culture to calcium ionophore A23187.

* * * * *